United States Patent [19]
Turner, II

[11] Patent Number: 5,137,025
[45] Date of Patent: Aug. 11, 1992

[54] NOMOGRAM FOR ELECTROCARDIOGRAPHIC INTERPRETATION AND METHOD OF USE

[76] Inventor: Henry H. Turner, II, 2702 Techwood Dr., Columbus, Ga. 31906

[21] Appl. No.: 628,600

[22] Filed: Dec. 17, 1990

[51] Int. Cl.$^5$ .......................................... A61B 10/00
[52] U.S. Cl. ..................................... 128/695; 33/1 C
[58] Field of Search ............... 128/630, 695, 696, 699; 33/1

[56] References Cited

U.S. PATENT DOCUMENTS

| | | | |
|---|---|---|---|
| 2,501,550 | 3/1950 | Tamagna et al. | 33/1 C |
| 3,686,764 | 8/1972 | Oesterritter | 33/1 C |
| 3,812,586 | 5/1974 | Itokawa | 33/1 C |
| 4,023,276 | 5/1977 | Furukawa et al. | 33/1 C |
| 4,030,486 | 6/1977 | Eastman | 33/1 C |
| 4,282,655 | 8/1981 | Tinman | 33/1 C |
| 4,550,502 | 11/1985 | Grayzel | 128/702 |
| 4,552,156 | 11/1985 | Jackson | 128/703 |
| 4,936,022 | 6/1990 | Grayzel | 33/664 |

OTHER PUBLICATIONS

Article reprinted from *Medizinische Monatschrift*, vol. 1, p. 781, 1947, written by Von Dr. med. E. Lepeschkin, entitled "Die Aktivitatsdauer des Herzmuskels" (QT- and ST-Dauer des Elektrokardiogramms) pp. 78-83.

Primary Examiner—William E. Kamm
Attorney, Agent, or Firm—Kilpatrick & Cody

[57] ABSTRACT

Nomograms for interpreting electrocardiograms. A Q line appears on the nomograms and may contain a series a calibrations relating to various cardiac rates. A P curve is oriented relative to the Q line for representing normal PR intervals for a particular age group. A T curve is oriented relative to the Q line for representation of normal QT intervals for the age group. The nomograms may feature a Q2 line oriented relative to Q line such that distances between the Q and Q2 lines for various cardiac rates equal the electrocardiogram distance for a cardiac cycle having that cardiac rate. The nomograms may feature a count 2 scale and/or a six second scale for independently determining cardiac rate, a Holter scale, and other information as desired. Complementary color schemes may be used for accentuating boundaries between, for instance, the area between the P and T curves and other areas on the nomograms.

60 Claims, 6 Drawing Sheets

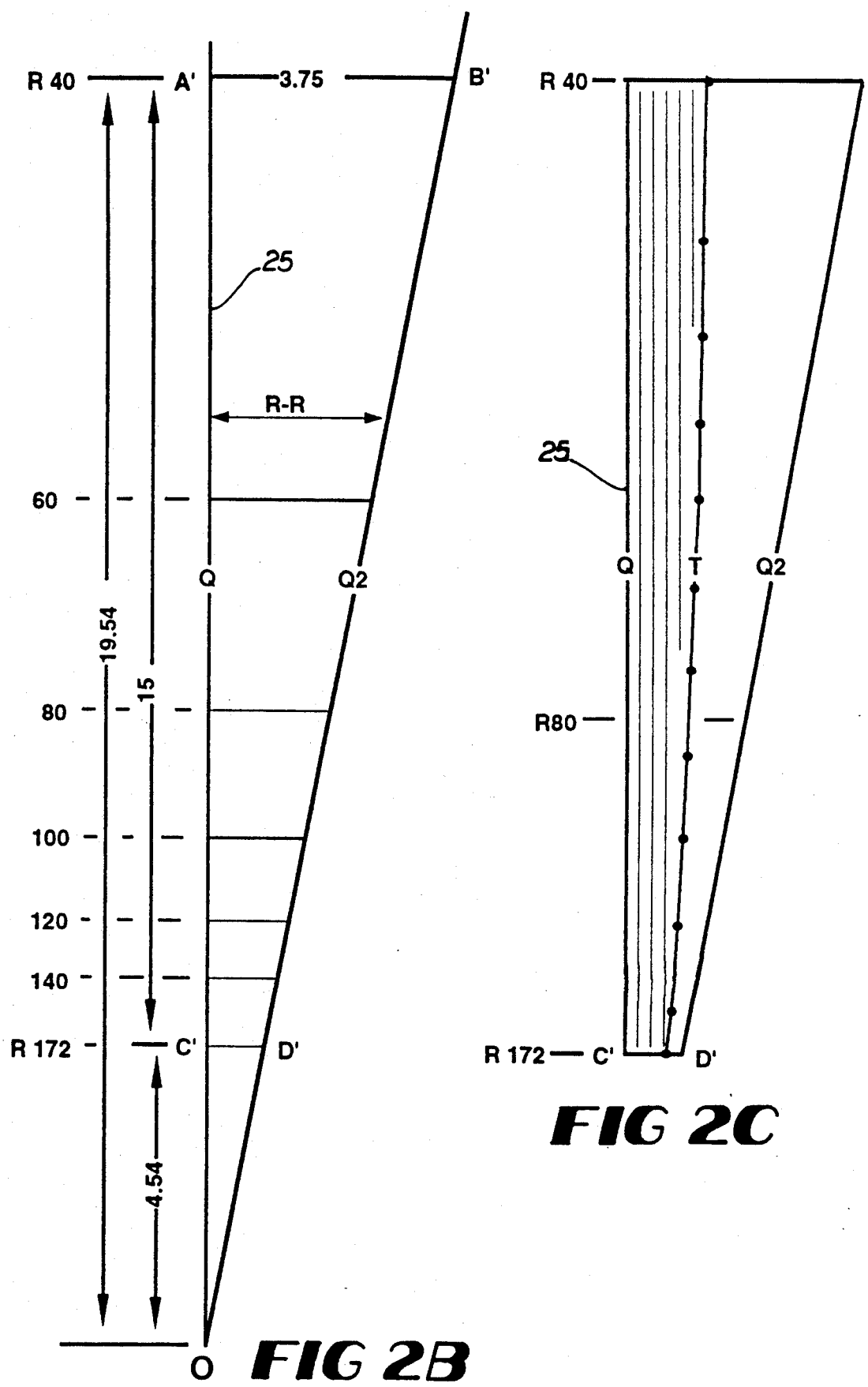

NOMOGRAM FOR ELECTROCARDIOGRAPHIC INTERPRETATION AND METHOD OF USE

The present invention relates to nomograms which may be used for interpretation of electrocardiograms.

BACKGROUND OF THE INVENTION

Electrocardiographic techniques provide graphic data regarding cardiac events using a number of electrodes placed in electrical contact with a patient's skin. The electrodes are connected to an electrical device which receives signals via the electrodes, amplifies them, and presents them typically on graph paper via electromechanical means. Typical present day electrocardiographic devices use hot filaments to burn a track on a strip of heat sensitive paper as the paper moves at constant speed. The filament is deflected up or down in accordance with variations of the signals associated with cardiac events.

Electrocardiographic paper is printed with a grid of vertical and horizontal lines at intervals of one millimeter, the distance between vertical lines representing four hundredths (0.04) second. Every fifth line is heavier, thereby making intervals of one-fifth (0.2) second. The paper is transported at a standard speed of 25 millimeters per second, the equivalent of 150 centimeters per minute. Horizontal distances on the paper thus represent time, and are generally referred to in units of time.

Cardiac events are obviously independent of the paper movement, and in any event typically do not exhibit the periodicity of the grid lines, so that graphic information transcribed on the paper (the electrocardiogram) is interpreted using the horizontal and vertical lines only as a gauge for estimation.

As shown in FIG. 1, a normal cardiac cycle as presented on an electrocardiogram consists, from left to right, of (1) a "P wave" associated with atrial contraction, (2) an interval of electrical neutrality, (3) the "QRS complex" associated with ventricular contraction, (4) another interval of neutrality, (5) the "T wave" associated with ventricular recovery, and (6) a period of neutrality ending when a successive "P wave" starts a new cycle. The term "R-R interval" is used to refer to the distance from a prominent point in a cycle to the corresponding point in the succeeding cycle, and, with normal regular rhythm, is equal in length to a cardiac cycle, as shown in FIG. 1. As generally accepted, the range of normal cardiac cycle frequency or cardiac rate extends from 60 to 100. The term "bradycardia" refers to cardiac rates below 60, and "tachycardia" refers to cardiac rates greater then 100.

Basic ECG interpretation techniques include the following:

(1) Measurement of cardiac rate in cycles per minute;

(2) Measurement of the PR interval (time from the beginning of the P wave to the beginning of the QRS complex);

(3) Measurement of the duration of the QRS complex; and (4) Measurement of the QT interval (time from the beginning of the QRS complex to the end of the T wave).

Prolongation of the PR interval or the QT interval beyond accepted standards for age and sex indicates disease. For example, a prolonged PR interval in a child may indicate rheumatic fever.

Conventional interpretation of electrocardiograms involves measurement of the duration of these intervals using the vertical lines of the printed electrocardiographic paper grid. Specially calibrated and generally opaque rulers are also conventionally employed. The intervals which are read using the grid or rulers may be compared with tables which represent a significant sample of patients, both with and without heart disease. The tables are typically arranged by age and (sometimes) by sex for normal and diseased hearts. Tables prepared by various authorities obviously vary. Two such tables, one for upper normal PR intervals and one for upper normal QT intervals, were prepared by R. Ashman and E. Hull and appear in their book, *Essentials of Electrocardiography*, 2nd edition, McMillan Company, New York, 1947, as reproduced in *The Electrocardiographic Test Book*, published by the American Heart Association in 1958, both of which are incorporated by this reference. Those tables are as follows:

TABLE 1

| | Upper Limits of Normal for QT Intervals | |
|---|---|---|
| RATE | Men and Children | Women |
| 40 | 0.49 | 0.50 |
| 43 | 0.48 | 0.49 |
| 46 | 0.47 | 0.48 |
| 48 | 0.46 | 0.47 |
| 50 | 0.45 | 0.46 |
| 52 | 0.45 | 0.46 |
| 55 | 0.44 | 0.45 |
| 40 | 0.49 | 0.50 |
| 43 | 0.48 | 0.49 |
| 57 | 0.43 | 0.44 |
| 60 | 0.42 | 0.43 |
| 63 | 0.41 | 0.42 |
| 67 | 0.40 | 0.42 |
| 71 | 0.39 | 0.41 |
| 75 | 0.38 | 0.39 |
| 80 | 0.37 | 0.38 |
| 86 | 0.36 | 0.37 |
| 93 | 0.35 | 0.36 |
| 100 | 0.34 | 0.35 |
| 109 | 0.33 | 0.33 |
| 120 | 0.31 | 0.32 |
| 133 | 0.29 | 0.30 |
| 150 | 0.28 | 0.28 |
| 172 | 0.26 | 0.26 |

TABLE 2

| | Upper Limits of Normal for PR Intervals | | | | |
|---|---|---|---|---|---|
| RATE | <70 | 71-90 | 91-110 | 111-130 | >130 |
| Large adults | 0.21 | 0.20 | 0.19 | 0.18 | 0.17 |
| Small adults | 0.20 | 0.19 | 0.18 | 0.17 | 0.16 |
| Children 14-17 | 0.19 | 0.18 | 0.17 | 0.16 | 0.15 |
| Children 7-13 | 0.18 | 0.17 | 0.16 | 0.15 | 0.14 |
| Children 1.5-6 | 0.17 | 0.165 | 0.155 | 0.145 | 0.135 |
| Children 0-1.5 | 0.16 | 0.15 | 0.145 | 0.135 | 0.125 |

The Ashman and Hull tables are utilized to prepare a preferred embodiment of age- and, where indicated, sex-specific nomograms according to the present invention.

Electrocardiographic interpretation using the paper grids or rulers, mentally noting the relevant interval and comparing, when necessary, to tabular data necessarily involves inaccuracies and induces error. For example, such devices only provide means for measurement of one value at a time so that, when needed, an interrupting reference must be made to the tables commonly at hand, causing loss of eye contact with the cycle in question on the EKG. Use of opaque rulers or strips also obstructs view of an appreciable portion of the electrocardiogram under interpretation. In any event, measurement of the intervals along an opaque straight edge may require multiple positioning: after a first positioning for rate measurement, a second positioning may be required for measurement of the PR interval, and a third for the QT interval, unless the P wave, the QRS complex, and the T wave are fortuitously well placed in relation to the prepared grid. With marginal values there is the further step or steps of accessing one or more tables for upper normal values according to age and, in some cases, sex. A persistent factor frequently contributing to inaccuracy, when scrutiny without measurement is relied on, is the random relationship of the inscription to the grid on the prepared paper. All of these factors introduce room for error.

SUMMARY OF THE INVENTION

The present invention provides, with one positioning of a transparent device, the ability to determine cardiac rate, immediate recognition of prolongation of the PR interval for different age groups, immediate recognition of prolongation of the QT interval for different age and sex groups, and means for measuring the PR and QT intervals using vertical linear calibrations on the device that correspond to time on the electrocardiogram. The electrocardiogram is seen in full context (not partially blocked out by an opaque ruler), accuracy is enhanced by eliminating mental adjustments for random grid relationship, and accessing tables for normal limits is only rarely required.

The present invention allows for interpretation of an electrocardiogram by applying an age-, and sometimes sex-, specific nomogram preferably formed of clear plastic material, which graphically presents data previously presented in tables. The graphic representation of such data on the nomogram allows the interpreter to place the nomogram on an electrocardiogram and quickly and accurately note, among other things, the cardiac rate, the PR interval, the duration of the QRS complex, and the QT interval. Each nomogram is preferably structured to allow interpretation of an electrocardiogram corresponding to one group or set of patients or individuals, such as for instance, children between birth and 1.5 years of age, children between 1.5 and 6 years as a second set, children ages 7 through 17 as a third set, and adults 18 and over as a fourth set. Preferably there are two such nomograms on a transparent sheet or plate of plastic, the nomograms oriented upside down with respect to each other, saving space by virtue of their triangular shape in the device thereby formed. Typically on such a device with two nomograms there is a scale for determining cardiac rate by measuring two cycles as represented on an electrocardiogram, means for determining cardiac rate by counting the number of cycles on a 15 centimeter (6 second) scale, and a scale for determining time between cardiac events and rate for a strip made at a slow inscription speed, such as a Holter electrocardiogram, with prominent markings of 6 and 12 seconds, to facilitate measurement of rate. Additional graphic data such as representation of a complete cycle properly positioned for interpretation and an electrocardiographic grid, continuous with the vertical lines for measuring QT intervals, may be included. On such a grid the upper ends of the vertical lines between the extremes of vertical lines may be at a slope, allowing a clear view of the tracing being measured. The device with two nomograms preferably also features complementary colors such as yellow and blue for ease of use and enhancement of boundaries with minimization of possibility of error in interpretation. Various arrangements of clear areas and tones of gray may be used instead of or along with colors.

BRIEF DESCRIPTION OF THE DRAWINGS

FIGS. 2A through 2C are schematic diagrams showing triangular relationships involved in preparing nomograms according to the present invention.

DETAILED DESCRIPTION OF THE DRAWINGS

Figure 1:
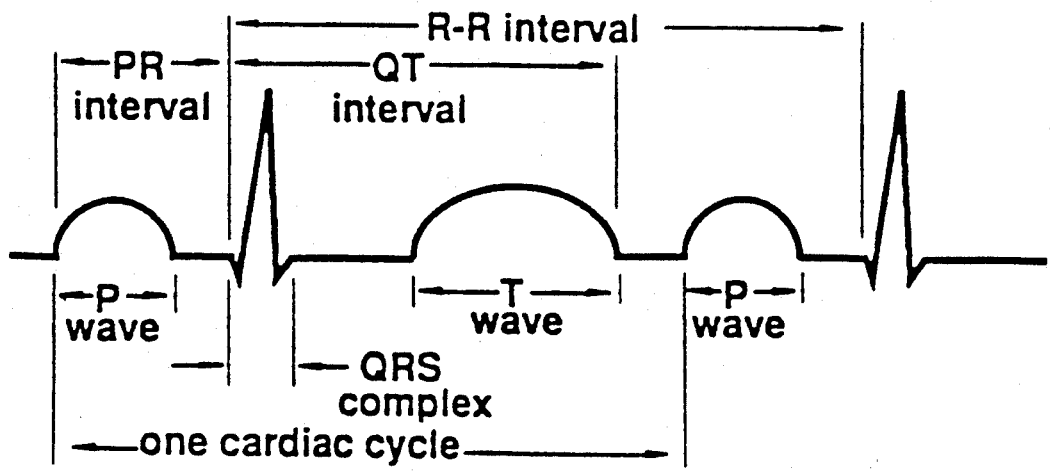
FIG. 1, as discussed above, is a graphic representation of a cardiac cycle as presented on a typical electrocardiogram.
Figure 2A:
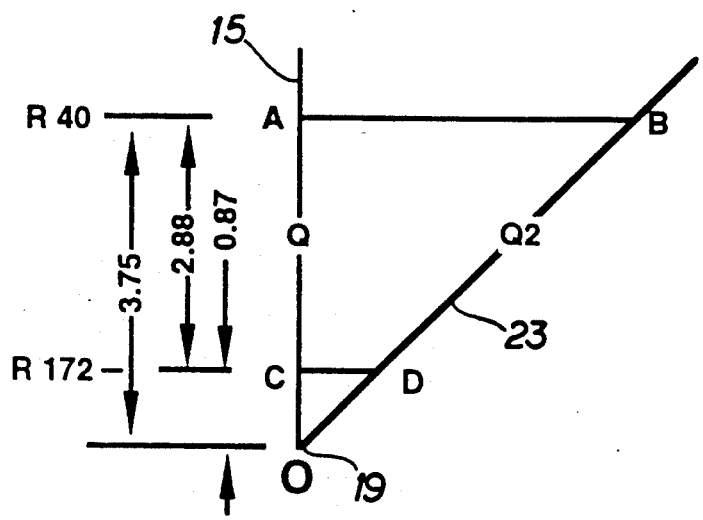

Theoretically, given the standard velocity for ECG transcription of 150 (60×2.5) centimeters per minute, the linear length of the cardiac cycle for any rate (R) is 150/R centimeters. In constructing a nomogram according to the present invention, as shown in FIGS. 2A–C, the length in centimeters for various cardiac rates may be marked along a Y-axis 15, so that, for instance, the rate of 172 is represented by a mark C 0.87 centimeters from Origin 19, and a rate of 40 is represented by a mark A 3.75 centimeters from Origin. One may then construct another, oblique line 23 from Origin 19 at an angle of forty five degrees, so that a line extending horizontally from the 40 rate mark on the Y-axis 15 to the oblique line 23 would be of equivalent length to the distance between Origin 19 and the 40 rate mark on the Y-axis. One may then place the triangular representation over an EKG tracing and translate the triangle on the EKG until corresponding points of successive cycles are aligned with the Y-axis and with the oblique line 23, respectively. The cardiac rate may then be interpolated using the rates and marks on the Y-axis 15. Unfortunately, however, the scale using a forty five degree triangle is too compressed for an adequate number and spacing of calibrations of cardiac rates in the direction of the Y-axis. Furthermore, the slope of the oblique line is greater than ideal for measurement of horizontal distances corresponding to time.

Because of the above described congestion, the triangle may be expanded vertically, preserving however the proportionality of all vertical measurements. The line segment CA in FIG. 2A may accordingly be changed to be represented in FIG. 2B by line segment C'A', with a new length of 15 centimeters, relief of congestion being thereby provided, along with enhanced sensitivity for transverse measurement. The expansion factor selected was the ratio of segment C'A' to segment CA, or 15/2.88, equal to 5.2121. The length 15 centimeters was chosen as preferable (but not necessary) since, in addition to relieving congestion, it was a convenient length for measuring rate, being one tenth the distance (150 centimeters) of standard propagation of an electrocardiogram in one minute. Line segments AB and CD, unchanged in length, were repositioned in FIG. 2B as line segments A'B' and C'D'. Truncating the triangle of FIG. 2B at the level for the rate 172 (the greatest rate in Ashman and Hull) yielded the quadrilateral A'B'C'D', a truncated right triangle, a prominent aspect of this invention.

Figure 4:
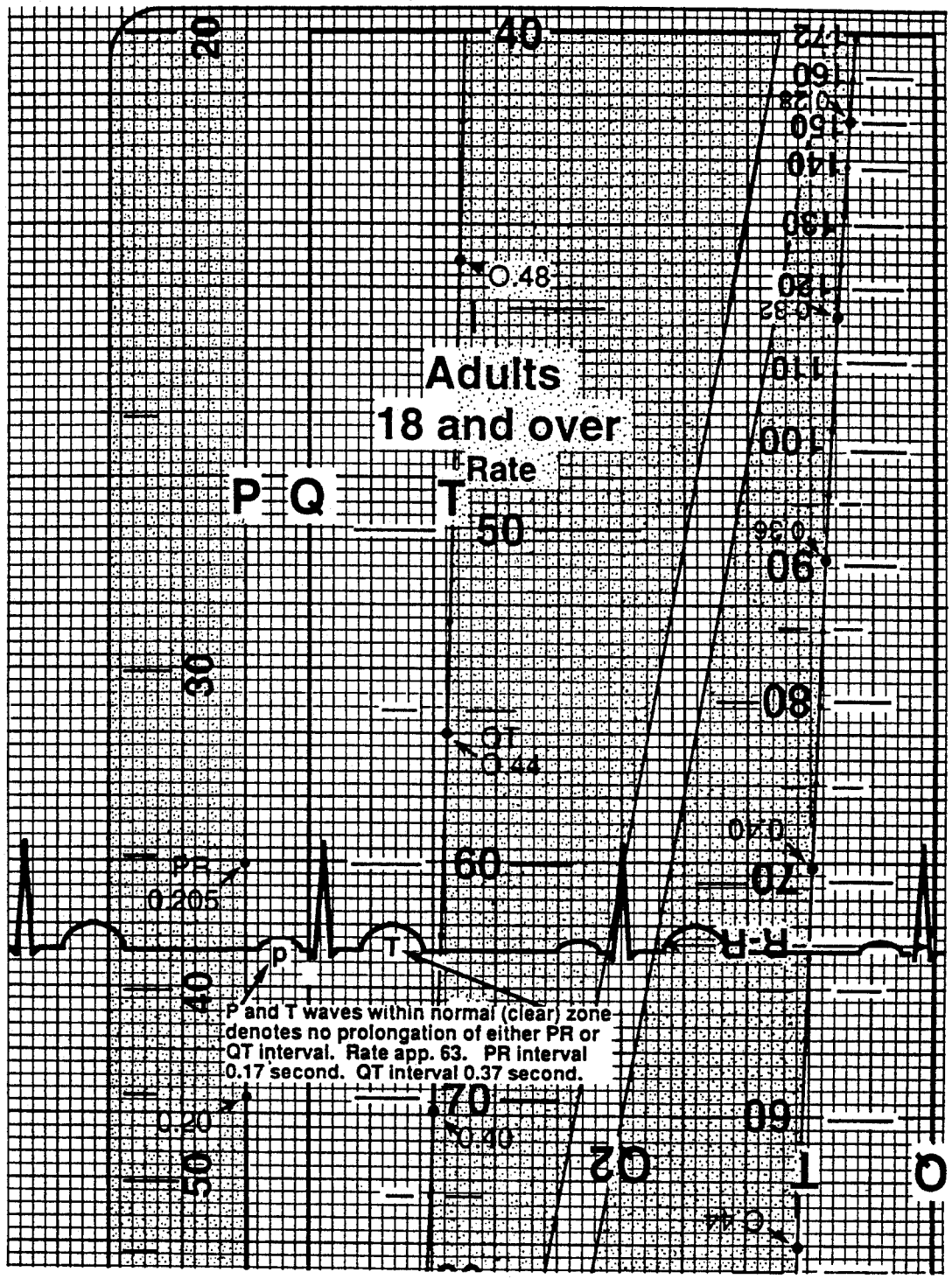
FIG. 4 shows a nomogram according to the present invention for adults 18 years and over placed over a normal EKG for interpretation.

The 15 centimeter line (A'C') on the nomogram is considered the Q line, and the other leg of the triangle is considered the Q2 line, as shown in FIGS. 2A-C. Q and Q2 lines are aligned with the beginnings of the QRS complexes of successive cycles while the Q line is maintained vertical on the electrocardiogram, as shown, for instance, in FIGS. 4-6. The cardiac rate may be interpolated using the cardiac rate marks or scale which appear near the T curve in FIGS. 4-6. In FIG. 4, for instance, the cardiac rate appears as approximately 63.

Nomograms according to the present invention are particularly useful for quick and accurate interpretation of PR intervals and QT intervals. The P curve on the preferred embodiments of each nomogram is derived from the upper normal values for PR intervals which appear in Table 2. Thus the 'average' P curve in FIGS. 4, 5, and 6 for adults is constructed from this table, since it includes values for large adults and small adults for rates below 70, 71-90, 91-110, 110-130, and over 130. In each 20 point range the value for large adults is 0.01 second greater than that for small adults. The average value for the two groups for each range thus varies from the respective value for either groups by five milliseconds. Values for rates less than 70 and more than 130 are given as 0.01 seconds greater than or less than the adjacent 20 point ranges respectively. Accordingly, the average value for each 20 point range is assigned to its midpoint and projected to the nomogram at its proper level. Values for rates less than 70 and greater than 130 are projected to rate levels for 60 and 130 respectively, and maintained to the extremes of rate represented by the nomogram, in accordance with the terminology 'below 70' and 'above 130' in Table 2. Upper normal limits for PR intervals for ages 7-13 and 14-17 also vary by the same 0.01 second, five milliseconds from the average, allowing the P curve to be constructed similarly. For practical purposes, the variation of milliseconds is not felt excessive. It can, however, be eliminated if so desired, as it is in the nomograms for age 0-1.5 and age 1.5-6 years in which PR values are projected to the nomograms directly from the table without averaging.

The P curve may be calibrated vertically, as shown in FIGS. 3, 4, 5, and 6, for measurement closer than 0.04 second.

The T curve may be constructed from Ashman and Hull's formula:

$$QT = K\log(10[C+k])$$

where $K=0.41$ for men and children, $K=0.42$ for women, $k=0.07$, and $C=RR$ (length of a cardiac cycle) in secs.

K being a linear constant, the value 0.415 represents average for adults and children of ages 7-17. QT values may be calculated accordingly and projected to the nomograms. The P and T curves may be labelled with calibrations for intervals less than 0.04 seconds, for more precise measurements. Thus, in FIG. 2C the T curve is marked by nodes of calibration for time at intervals of 0.01 seconds, using the above formula rearranged as:

$$C = antilog(QT/K - 1) - k.$$

Nomograms of the present invention preferably use complementary translucent colors for ease of interpretation. According to one scheme, yellow may be used between the P and T curves to denote the area where normal values are found, with areas beyond the 'normal' zone a complementary blue. It is recognized in the printing arts that translucent yellow interferes less with transmission of visually perceived light than other colors. Such a scheme of complementary colors is restful to the eye and allows for quick and reliable discrimination between one area and the next on the nomogram. Contrast at borders need not be limited to complementary colors, however, but may be produced by judicious use of other colors or by shading or by a state of clearness, with absence of both color and shading.

Figure 3:
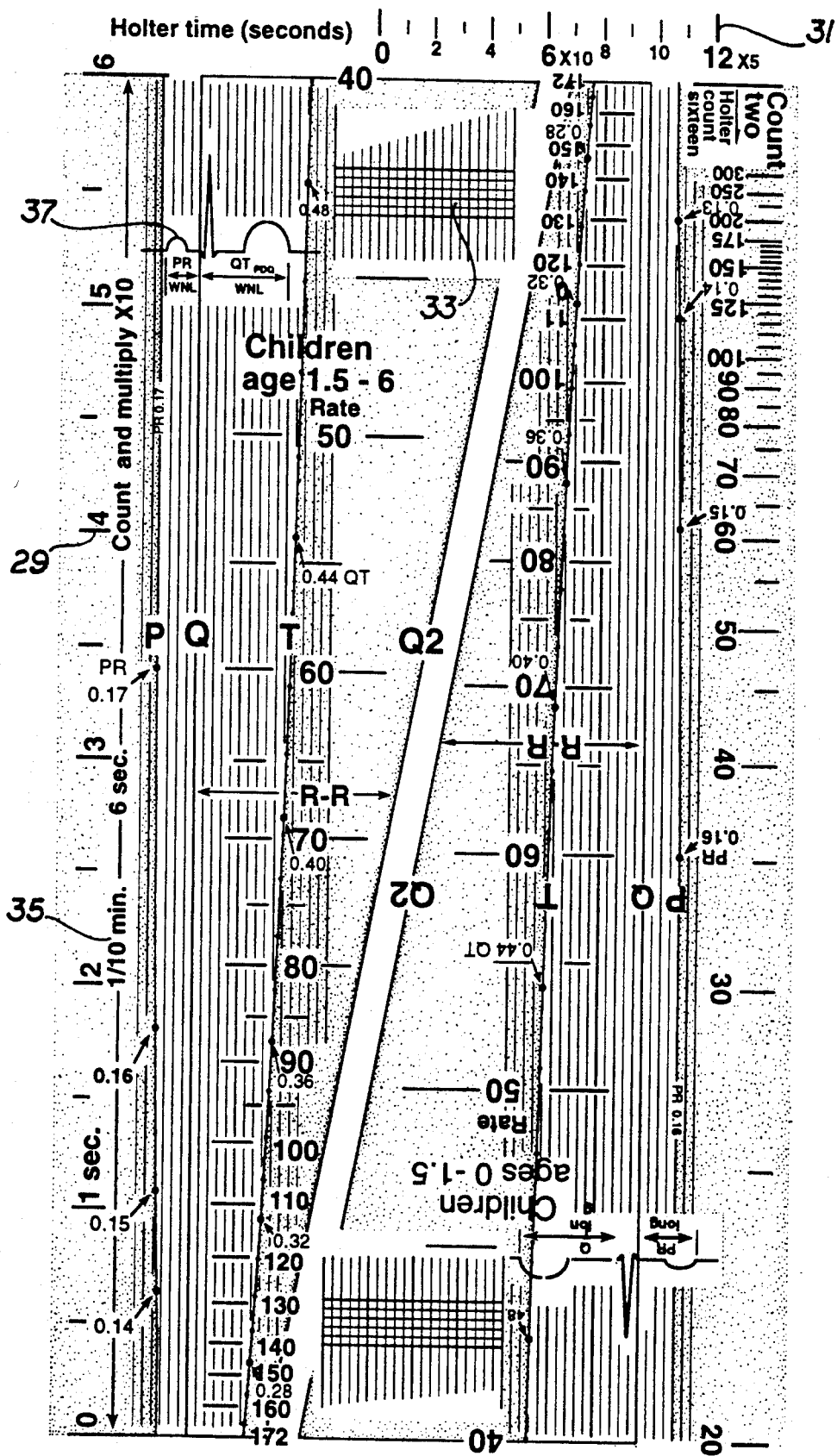
FIG. 3 shows two nomograms on a transparent plate, or template, one for interpretation of cardiac events of children between birth and 1.5 years, and one for children between 1.5 and 6 years of age.

Two nomograms, each representing a set of indicia and each having a P curve for upper normal PR values for an age group and a T curve for upper normal QT values for an age and/or sex group, are preferably graphically represented on a rectangular or other desirably shaped transparent device, or plate, there being represented on each such device, for instance, data for children between birth and 1.5 years, and between 1.5 and 6 years, or children between 7 and 17 years and adults 18 and over. Other additional features are also preferably added, including the following as shown in FIG. 3: (1) a conventional "Count 2" scale 27 for determination of rate by measuring two complexes; (2) a scale 29 for measuring time is seconds; (3) a scale 31 for measuring rate and time values of an electrocardiogram made with a slow inscription speed, such as a Holter monitor herein represented (a device with transcription speed a fraction of standard, such as ¼ that of the standard, showing all complexes for an extended period, such as 24 hours), there being on the Holter scale calibrations for time, with 6 and 12 second intervals accentuated, for multiplying ×10 or ×5 in measuring rate; (4) a grid 33 checkered in accordance with the grid of electrocardiographic paper, herein continuous with the vertical markings for measuring the QT interval, and with sloping upper margin of vertical lines; (5) a 15 centimeter scale 35 for counting the number of complexes which occur in six seconds for multiplication by 10; and (6) a representation 37 on each nomogram of the cardiac cycle with Q of Q2 lines positioned for interpretation.

Accordingly, cardiac rate may be measured using any of three methods with such a transparent device: (1) using the conventional "Count 2" scale; (2) counting complexes on the six second scale and multiplying by 10; and (3) aligning the age- and, when indicated, sex-specific nomogram so that the Q and Q2 lines overlie the beginnings of successive QRS complexes and reading the rate on the scale. A closer reading may be made by translating the nomogram up or down so that the closer calibrations on the P curve or on the T curve bear on the electrocardiogram at the beginning of the P wave or end of the T wave.

Figure 5:
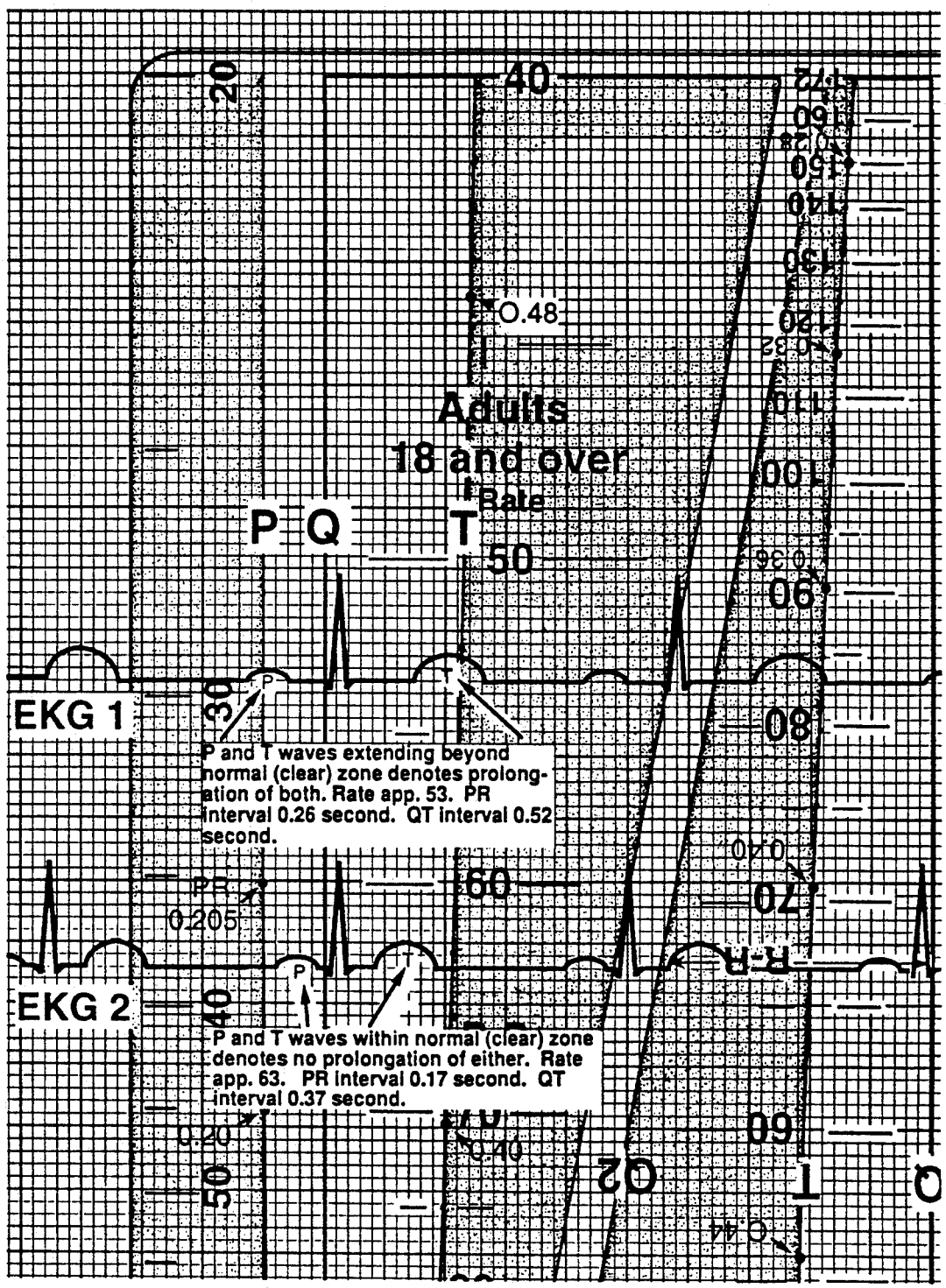
FIG. 5 shows a nomogram according to the present invention placed over a first abnormal EKG and a second normal EKG for interpretation.
Figure 6:
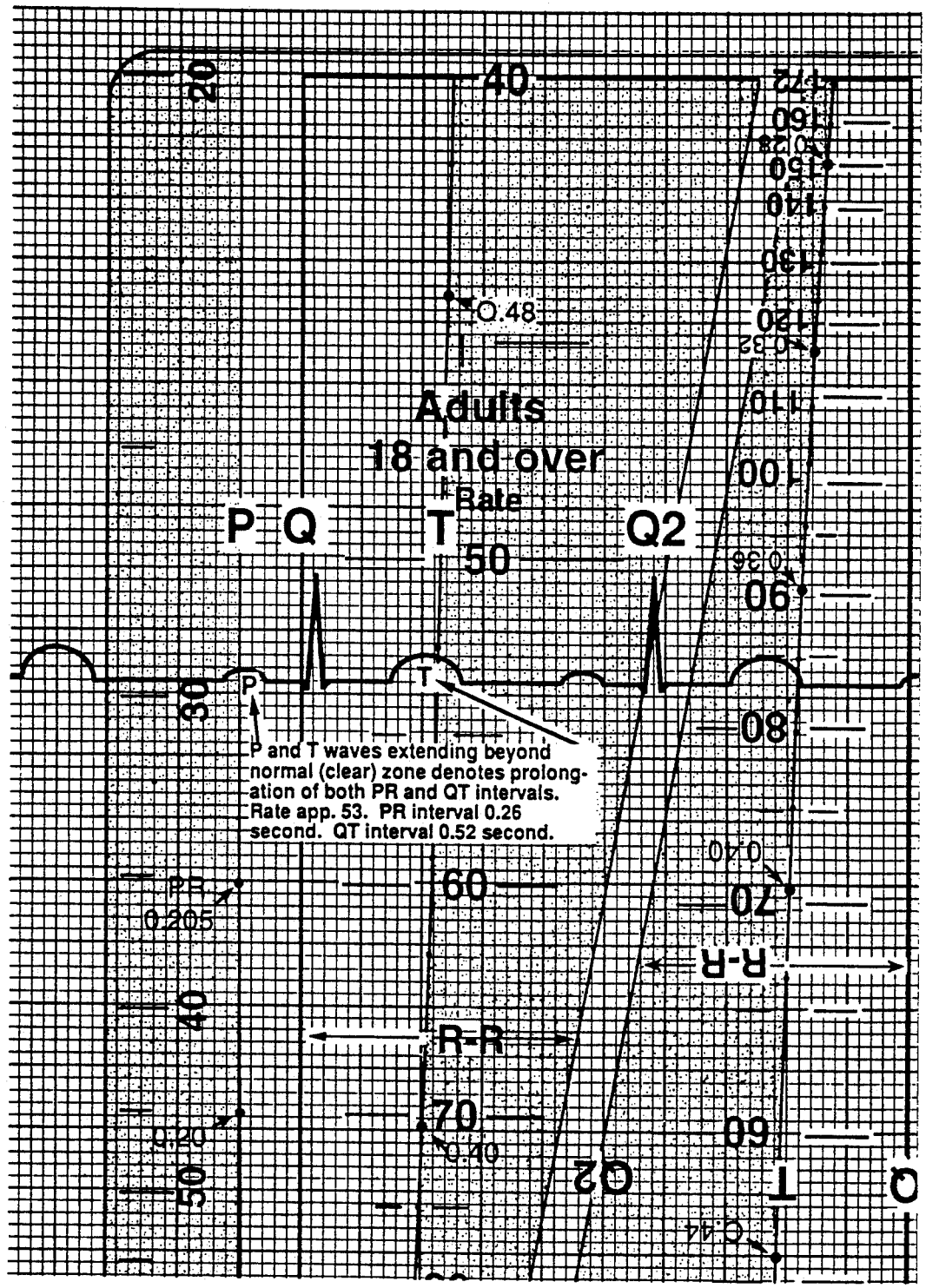
FIG. 6 shows a nomogram according to the present invention placed over a second abnormal EKG for interpretation.

In use, as shown in FIGS. 4, 5, and 6, the Q and Q2 lines are aligned with the beginnings of successive QRS complexes while the Q line is aligned vertically on the electrocardiographic grid. The cardiac rate may be read directly from the vertically oriented markings for rate. The user may instantly determine whether the PR interval is prolonged by noting whether any portion of the P wave extends beyond the P curve, as in the upper trace of FIG. 5 and in FIG. 6.

The foregoing is provided for purposes of explanation an illustration of a preferred embodiment of the present invention, as adapted to the set of data from Ashman and Hull. Adaptations to other data and modifications may be made without departing from the scope or spirit of the invention.

What is claimed is:

1. A nomogram for graphic representation of variation in upper normal values of electrocardiographic PR and QT intervals for groups of individuals, comprising:
   (a) a transparent substrate; and
   (b) at least one set of indicia placed on the substrate, corresponding to an age group and, when desired, sex group, and including a range of cardiac rates reflecting bradycardia and tachycardia conditions for such individuals, comprising:
      (i) a Q line;
      (ii) a series of calibrations on the Q line, each corresponding to a predetermined cardiac rate;
      (iii) a P curve to the left of the Q line so oriented that the horizontal distance between each calibration on the line Q and the P curve equals the upper normal limit for the PR interval corresponding to the associated rate and age group;
      (iv) a T curve to the right of the Q line so oriented that the horizontal distance between each calibration on the line Q and the T curve equals the upper normal limit for the QT interval corresponding to the associated rate and age group and, when pertinent, sex group.

2. The nomogram of claim 1 in which the extremes of the Q line correspond generally to the extremes of rate reflected by the indicia.

3. The nomogram of claim 2 in which the Q line has a first end that corresponds to a cardiac rate of 172 and a second end that corresponds to a cardiac rate of 40.

4. The nomogram of claim 1 in which the Q line is 15 centimeters long.

5. The nomogram of claim 1 further comprising a plurality of lines parallel to and extending to the left of the Q line at intervals of 0.04 second for measuring PR intervals.

6. The nomogram of claim further comprising a plurality of lines parallel to and extending to the right of the Q line at intervals of 0.04 second for measuring QT intervals.

7. The nomogram of claim 1 which contains at least two sets of indicia.

8. The nomogram of claim 1 further comprising a scale adapted for alignment with the electrocardiogram to read a cardiac rate that corresponds to the length of two cardiac cycles.

9. The nomogram of claim 1 further comprising a 15 centimeter linear scale adapted for alignment with electrocardiogram to measure time between selected events and to count the number of cardiac cycles occurring in six seconds in order to determine cardiac rate.

10. The nomogram of claim 1 further comprising a first color placed on the nomogram between the P and T curves, and a second color placed in other areas.

11. The nomogram of claim 10 in which the first and second colors are visually complementary.

12. The nomogram of claim 10 in which the first color is yellow.

13. The nomogram of claim 1 in which the area between the P and T curves contrasts in shade with other adjacent areas.

14. The nomogram of claim 1 further comprising a scale for measuring time and rate on an electrocardiogram made at a speed of recording slower than conventional speeds, such as by a Holter monitor.

15. The nomogram of claim 14 having a scale being so arranged as to accentuate intervals corresponding to 0.1 and 0.2 minutes.

16. The nomogram of claim 1 further comprising a grid corresponding to electrocardiographic paper grid for superimposition on an electrocardiogram.

17. The nomogram of claim 16 having a grid so positioned that its vertical lines are continuous with the plurality of the lines parallel to the Q line for measuring time, providing thereby a longer uninterrupted series of such lines.

18. The nomogram of claim 1 further comprising calibrations on at least one of the P and T curves for measuring increments of distance from the Q line of less than 0.04 second, such as 0.01 second.

19. The nomogram of claim 7 further comprising two generally triangular nomograms so arranged that each is upside down (rotated 180 degrees) with respect to the other, a conservation of space being thereby obtained.

20. The nomogram of claim 1 in which the distances of the calibrations on the Q line from a common reference point on an extension of the Q line are inversely proportional to their respective corresponding rates.

21. A device for interpreting an electrocardiogram, comprising:
   (a) a transparent substrate;
   (b) at least one set of indicia placed on the substrate, corresponding to an age group of individuals, and if desired, a sex group of individuals, and including a range of cardiac rates reflecting bradycardia and tachycardia conditions for such individuals, comprising:
      (i) a Q line;
      (ii) a plurality of markings corresponding to cardiac rates;
      (iii) a Q2 line oriented at a predetermined angle from the Q line so that the horizontal distances between the Q and the Q2 line, at predetermined points on the Q line, correspond to distances on the electrocardiogram for cardiac cycles whose rates correspond to the points on the Q line;
      (iv) a P curve oriented with respect to the Q line such that, for predetermined rates on the Q line, the perpendicular distances from the Q line to the P curve correspond to a statistically derived distance for upper normal PR intervals for the associated rate and age group; and
      (v) a T curve oriented with respect to the Q line such that, for predetermined rates on the Q line, the horizontal distance from the Q line to the T curve corresponds to a statistically derived distance for upper normal QT interval for the associated rate and age, and, when indicated, sex.

22. The nomogram of claim 21 in which the extremes of the Q line correspond generally to values approaching the extremes of rate reflected by the corresponding indicia.

23. The nomogram of claim 21 in which the Q line is 15 centimeters long.

24. The nomogram of claim 21 in which the Q line has a first end that corresponds to a cardiac rate of 172 and a second end that corresponds to a cardiac rate of 40.

25. The nomogram of claim 21 further comprising markings to indicate cardiac rates corresponding to distances between the Q and Q2 lines.

26. The nomogram of claim 21 further comprising markings adjacent to the P curve to indicate the length in seconds of upper normal PR intervals.

27. The nomogram of claim 21 further comprising markings adjacent to the T curve to indicate the length in seconds of upper normal QT intervals.

28. The nomogram of claim 21 which contains at least two sets of indicia.

29. The nomogram of claim 21 further comprising a scale which may be aligned with the electrocardiogram to read a cardiac rate that corresponds to the length on the electrocardiogram of two cardiac cycles.

30. The nomogram of claim 21 further comprising a 15 centimeter linear scale which may be aligned with the electrocardiogram to measure time between selected events and to count the number of cardiac cycles occurring in six seconds in order to determine cardiac rate.

31. The nomogram of claim 21 further comprising a first color placed on the nomogram between the P and T curves, and a second color placed in other areas.

32. The nomogram of claim 31 in which the first and second colors are visually complementary.

33. The nomogram of claim 31 in which the first color is yellow.

34. The nomogram of claim 21 further comprising a color placed on the nomogram in the area between the P and T curves for rendering more distinct the boundaries between that area and other areas, the color effecting less light absorption than other areas on the nomogram.

35. The nomogram of claim 21 in which the area between the P and T curves contrasts in shade with other adjacent areas.

36. The nomogram of claim 21 further comprising a plurality of parallel lines placed one millimeter apart between the extending beyond the P and Q2 line, for reading time on the electrocardiogram.

37. The nomogram of claim 21 further comprising a scale for measuring time and rate on an electrocardiogram made at a speed of recording slower than conventional speed, such as by a Holter monitor.

38. The nomogram of claim 37 being so arranged as to highlight or accentuate intervals corresponding to 0.1 minute and 0.2 minute.

39. The nomogram of claim 21 further comprising a grid corresponding to electrocardiographic paper grid for superimposition on an electrocardiogram.

40. The nomogram of claim 39 having a grid so positioned that its vertical lines are continuous with the plurality of the lines parallel to the Q line for measuring time, providing thereby a longer uninterrupted series of such lines.

41. The nomogram of claim 39 having a grid so shaped that the upper extremities of its vertical lines form a slope, to allow for a clearer view of the electrocardiogram being measured.

42. The nomogram of claim 21 further comprising calibrations on at least one of the P and T curves for measuring increments of distance from the Q line of less than 0.04 second, such as 0.01 second.

43. The nomogram of claim 21 further comprising two generally triangular nomograms so arranged that each is upside down (rotated 180 degrees) with respect to the other, a conservation of space being thereby obtained.

44. The nomogram of claim 21 further comprising markings to indicate cardiac rates corresponding to horizontal distances between the Q and Q2 lines.

45. The nomogram of claim 21 in which the distances of the calibrations on the Q line from a common reference point on an extension of the Q line are inversely proportional to their respective corresponding rates.

46. A nomogram for graphic representation of variation in upper normal values of electrocardiographs for PR and QT intervals for groups of individuals comprising:
(a) a translucent substrate; and
(b) at least two sets of indicia placed on the substrate, each set corresponding to an age group and, when desired, sex group, and including a range of cardiac rates reflecting bradycardia and tachycardia conditions for such individuals, comprising:
(i) a Q line;
(ii) a series of calibrations on the Q line, each corresponding to a predetermined cardiac rate, the distances of the calibrations from a common reference point on an extension of the Q line being inversely proportional to the corresponding rates;
(iii) a Q2 line oriented relative to the Q line so that the horizontal distance between the Q and Q2 lines for each calibration on the Q line equals the length of a cardiac cycle having a rate corresponding to the calibration;
(iv) a P curve oriented relative to the Q line so that the horizontal distance between the Q line and the P curve for each calibration on the Q line equals the upper normal limit for the PR interval for the associated rate and age group; and
(v) a T curve oriented relative to the Q line so that the horizontal distance between the Q line and the T curve for each calibration on the Q line equals the upper normal limit for the QT interval for the associated rate and age group and, when indicted, sex group.

47. The nomogram of claim 46 further comprising a first color placed on the nomogram between the P and T curves, and a second color placed on the nomogram in other locations.

48. The nomogram of claim 47 in which the first and second colors are visually complementary.

49. The nomogram of claim 47 in which the first color is yellow.

50. The nomogram of claim 46 further comprising a color placed on the nomogram in the area between the P and T curves for rendering more distinct the boundaries between that area and other areas, the color effecting less light absorption than other areas on the nomogram.

51. The nomogram of claim 46 further comprising a plurality of parallel lines placed one millimeter apart between and adjacent to the P and T curves and parallel to the Q line, for reading time on an electrocardiogram.

52. A method for interpreting an electrocardiogram, comprising the steps of:
(a) providing a nomogram bearing at least two sets of indicia, each set corresponding to an age group of individuals and, when desired, sex group, and including a range of cardiac rates reflecting bradycardia and tachycardia conditions for such individuals, comprising:
  (i) a Q line;
  (ii) a series of calibrations on the Q line, each corresponding to a predetermined cardiac rate, the distances of the calibrations from a common reference point on an extension of the Q line being inversely proportional to the corresponding rates;
  (iii) a Q2 line oriented relative to the Q line so that the horizontal distance between the Q and Q2 line for each calibration on the Q line equals the length of an electrocardiographic cardiac cycle having a cardiac rate corresponding to the calibration;
  (iv) a P curve oriented relative to the Q line so that the horizontal distance between the Q line and the P curve for each calibration on the Q line equals the upper normal limit for the corresponding rate and age group; and
  (v) a T curve oriented relative to the Q line so that the horizontal distance between the Q line and the T curve for each calibration on the Q line equals the upper normal limit for the QT interval for the corresponding rate and age group and, when indicated, sex group;
(b) aligning the nomogram on the electrocardiogram so that the Q line is vertically oriented with respect to the horizontal markings of the grid on the electrocardiogram;
(c) aligning the Q line with the beginning of a selected cycle of the electrocardiogram so that the Q2 line intersects the beginning of the succeeding cycle; and
(d) noting the cardiac rate.

53. The method of claim 52 further comprising the step of noting whether the P wave of the selected cycle extends beyond the P curve and determining whether the PR interval is prolonged.

54. The method of claim 52 further comprising the step of noting whether the T wave of the selected cycle extends beyond the T curve and determining whether the QT interval of the selected cycle is prolonged.

55. A method for interpreting an electrocardiogram, comprising the steps of:
(a) providing a nomogram bearing at least one set of indicia, each set corresponding to an age group of individuals and, when desired, sex group, and including a range of cardiac rates reflecting bradycardia and tachycardia conditions for such individuals, comprising:
  (i) a Q line;
  (ii) a series of calibrations on the Q line, each corresponding to a predetermined cardiac rate;
  (iii) a P curve oriented relative to the Q line so that the horizontal distance between the Q line and the P curve for each calibration on the Q line equals the upper normal limit for the PR interval of the related rate and age group; and
  (iv) a T curve oriented relative to the Q line so that the horizontal distance between the Q line and the T curve for each calibration on the Q line equals the upper normal limit for the QT interval of the related rate and age group and, where indicated, sex group;
(b) determining the cardiac rate represented the electrocardiogram;
(c) aligning the nomogram on the electrocardiogram so that the Q line is vertically oriented with respect to the grid on the electrocardiogram;
(d) aligning the Q line with the beginning of a selected QRS complex of the electrocardiogram, and translating the nomogram vertically for proper rate; and
(e) noting whether the P and T waves of the complex extend beyond the P and T curves in order to determine whether the electrocardiogram represents prolonged PR and QT intervals.

56. The method of claim 55 in which the nomogram contains a count two scale and the cardiac rate is determined using the count two scale.

57. The method of claim 55 in which the nomogram contains a six second scale and the cardiac rate is determined using the six second scale.

58. A method for interpreting an electrocardiogram, comprising the steps of:
(a) providing a nomogram bearing at least one set of indicia and corresponding to an age group of individuals and, when indicated, sex group, and including a range of cardiac rates reflecting bradycardia and tachycardia conditions for such individuals, comprising:
  (i) a Q line;
  (ii) a series of calibrations on the Q line, each corresponding to a predetermined cardiac rate;
  (iii) a P curve to the left of the Q line so oriented that the horizontal distance from each calibration on the line Q to the P line equals the upper normal limit for the PR interval corresponding to the associated rate and age group;
  (iv) a T curve to the right of the Q line so oriented that the horizontal distance from each calibration on the Q line to the T curve equals the upper normal limit for the QT interval corresponding to the associated rate and age group and, when pertinent, sex group;
(b) determining the rate of the electrocardiogram;
(c) aligning the nomogram on the electrocardiogram so that the Q line is vertically oriented with respect to the horizontal markings of the grid on the electrocardiogram;
(d) aligning the Q line with the beginning of a selected cycle of the electrocardiogram at the proper rate level on the Q line; and
(e) noting whether the P and T waves of the cycle extend beyond the P and T curves in order to determine whether the electrocardiogram represents unprolonged or prolonged PR and QT intervals.

59. A method for interpreting an electrocardiogram, comprising the steps of:
(a) providing a nomogram bearing at least one set of indicia and corresponding to an age group of individuals and, when indicated, sex group, and including a range of cardiac rates reflecting bradycardia and tachycardia conditions for such individuals, comprising:
  (i) a Q line;
  (ii) a series of calibrations on the Q line, each corresponding to a predetermined cardiac rate;
  (iii) a P curve to the left of the Q line so oriented that the horizontal distance from each calibration on the line Q to the P curve equals the upper normal limit for the PR interval corresponding to the associated rate and age group;
(b) determining the rate of the electrocardiogram;

(c) aligning the nomogram on the electrocardiogram so that the Q line is vertically oriented with respect to the horizontal markings of the grid on the electrocardiogram;

(d) aligning the Q line with the beginning of a selected cycle of the electrocardiogram at the proper rate level on the Q line; and (e) noting whether the P wave of the cycle extends to the left of the P curve to determine whether the electrocardiogram represents prolonged PR interval.

60. A nomogram for graphic representation of variation in upper normal values for electrocardiographic PR intervals for various age groups of individuals, comprising:

(a) a transparent substrate; and (b) at least one set of indicia placed on the substrate, corresponding to an age group of individuals and, when indicated, sex group, and including a range of cardiac rates reflecting bradycardia and tachycardia conditions for such individuals, and comprising:

(i) a Q line;

(ii) a series of calibrations on the Q line, each corresponding to a predetermined cardiac rate; and (iii) a P curve to the left of the Q line so oriented that the horizontal distance between each calibration on the line Q and the P curve equals the upper normal limit for the PR interval corresponding to the associated rate and age group.

* * * * *

UNITED STATES PATENT AND TRADEMARK OFFICE
CERTIFICATE OF CORRECTION

PATENT NO. : 5,137,025

DATED : August 11, 1992

INVENTOR(S) : Henry H. Turner, II

It is certified that error appears in the above-identified patent and that said Letters Patent is hereby corrected as shown below:

Column 7, line 7, delete "an" and insert --and--

Column 7, line 49, after "claim" insert --1--

Signed and Sealed this

Twenty-third Day of November, 1993

Attest:

BRUCE LEHMAN

*Attesting Officer*     *Commissioner of Patents and Trademarks*